(12) United States Patent
Kawano

(10) Patent No.: US 6,387,811 B1
(45) Date of Patent: May 14, 2002

(54) METHOD FOR DETECTING SCRATCH OF AN INSULATING FILM

(75) Inventor: Hiroyuki Kawano, Tokyo (JP)

(73) Assignee: Oki Electric Industry Co, Ltd., Tokyo (JP)

( * ) Notice: Subject to any disclaimer, the term of this patent is extended or adjusted under 35 U.S.C. 154(b) by 0 days.

(21) Appl. No.: 09/612,461

(22) Filed: Jul. 7, 2000

(30) Foreign Application Priority Data

Mar. 13, 2000 (JP) ...................................... 2000-068775

(51) Int. Cl.[7] .............................................. H01L 21/302
(52) U.S. Cl. ........................ 438/691; 438/692; 438/751
(58) Field of Search .................................. 438/691, 737, 438/738, 692, 751, 8

(56) References Cited

U.S. PATENT DOCUMENTS

| | | |
|---|---|---|
| 5,514,245 A | 5/1996 | Doan et al. |
| 5,697,992 A | 12/1997 | Ueda et al. |
| 5,913,712 A | 6/1999 | Molinar |
| 6,258,437 B1 * | 7/2001 | Jarvis ......................... 428/137 |

FOREIGN PATENT DOCUMENTS

JP 06021181 A 1/1994

OTHER PUBLICATIONS

Wolf et al "Silicon Processing for the VLSI Era, vol. 1", Lattice Press, Calif. p. 534. (1986).*

* cited by examiner

*Primary Examiner*—Caridad Everhart
(74) *Attorney, Agent, or Firm*—Rabin & Berdo, P.C.

(57) ABSTRACT

In a device having a structure in which a silicon oxide film, a silicon nitride film, and a silicon oxide film are layered on a silicon substrate in that order from a bottom position, CMP polishing is performed in order for a top layer of a silicon oxide film to residually exist. An etchant for selectively etching a silicon nitride film only is then used. Only a nitride film in a scratched portion, the depth of which is deeper than the depth of the silicon oxide film, is selectively etched, and only the scratch, the depth of which is deeper than the depth of the residual film of the silicon oxide film, is exposed.

11 Claims, 2 Drawing Sheets

METHOD FOR DETECTING SCRATCH OF AN INSULATING FILM

BACKGROUND OF THE INVENTION

1. Field of the Invention

The present Invention relates to failure analysis technology in a semiconductor device fabrication process, and more especially to a method for improving detection sensitivity of a scratch (polish scratch) caused in a chemical mechanical polishing process of a fabrication method of the semiconductor device.

2. Description of Related Art

In recent years, new shrinking technology has been developed as development of high performance and highly integrated semiconductor integrated circuits (LSI) progresses. Chemical Mechanical Polishing (CMP) is one such process, and is applied to such processes as forming built-in wiring patterns and planalizing insulating films in a multi-layer interconnection process.

In general, CMP of the insulating film is performed by a chemical mechanical polishing process using fine particles contained in a slurry (polishing liquid). Polishing is accelerated owing to a cooperative process using a chemical etching agent such as an alkali liquid contained in the slurry. A polishing process with good evenness becomes possible, owing to a balance between the mechanical process and the chemical process. The fine particles contained in the slurry are particles of alumina, silica, and so forth having a particle diameter of several tens to several hundred nm, and liquid containing potassium hydroxide (KOH) or ammonium hydroxide ($NH_4OH$), etc. is employed as a chemical component.

However, in CMP, a scratch in a lower base layer can be caused due to fine particles of the slurry used as polishing material. Although it is recognized that a scratch, similar to a failure of a pattern and the particle might cause a lower yield rate, it has been extremely difficult not only to identify a scratch from the particles adhered in a process other than the polishing process, but also to detect itself. Thus, it has not been possible to analyze a correlation between yield rate and scratches since it was impossible to investigate a particle occurrence mechanism and it has been insufficient to devise a countermeasure to the scratch.

SUMMARY OF THE INVENTION

In a device having a structure in which a silicon oxide film, a silicon nitride film, and a silicon oxide film are layered on a silicon substrate in that order from a bottom position, CMP polishing is performed in order for a residual top layer of the oxide film to exist, and then an etchant for selectively etching a silicon nitride film is applied. A nitride film in a scratch portion, the depth of which is deeper than the depth of the oxide film, is only etched selectively, and only the scratch, the depth of which is deeper than the depth of the residual film of the oxide film, is exposed.

Further, in the other invention, a device having a structure in which a silicon oxide film and a silicon nitride film are layered repeatedly, performs CMP polishing in order for a residual top layer of the oxide film to remain, and then treats a nitride film using a selective etching liquid. Only a nitride film in a scratch portion, the depth of which is deeper than the depth of the residual film of the oxide film, is selectively etched, and only the scratch, the depth of which is deeper than the depth of the residual film of the oxide film and also reaches to respective nitride films, is exposed.

BRIEF DESCRIPTION OF THE DRAWINGS

The present invention will be understood more fully from the detailed description given below, in conjunction with the accompanying drawings.

DETAILED DESCRIPTION OF THE INVENTION

The invention will now be described based on the preferred embodiments. This does not intend to limit the scope of the present invention, but exemplify the invention. All of the features and the combinations thereof described in the embodiments are not necessarily essential to the invention.

Figure 1:
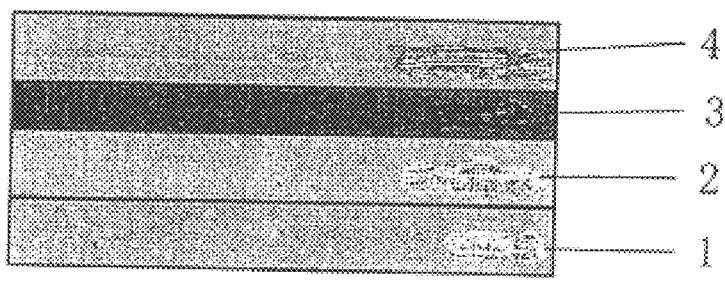
FIG. 1 is a sectional view of a fabricated specimen for explanation of the first preferred embodiment of the present invention, and illustrates a structure in which the top layer of a silicon oxide film is formed.
Figure 2:
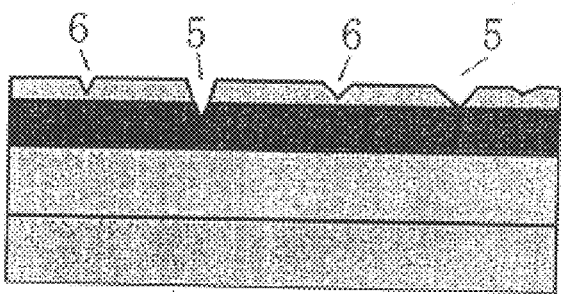
FIG. 2 is a sectional view of a fabricated specimen for explanation of the first preferred embodiment of the present invention, and illustrates scratches caused after CMP polishing.
Figure 3:
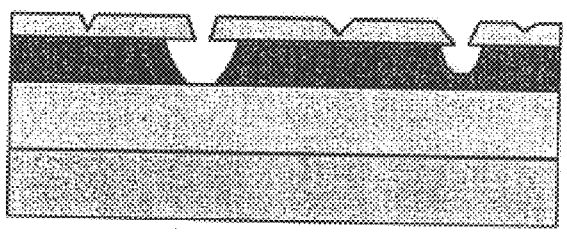
FIG. 3 is a sectional view of a fabricated specimen for explanation of the first preferred embodiment of the present invention, and illustrates etching of scratch portions.
Figure 4:
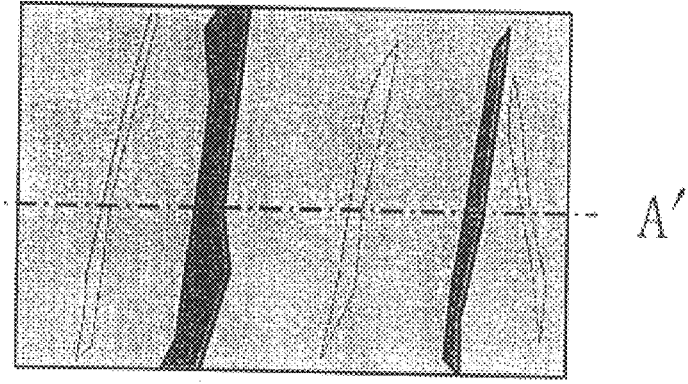
FIG. 4 is a sectional view of a fabricated specimen for explanation of the first preferred embodiment of the present invention, and illustrates a shape after etching the scratched portions.

FIGS. 1 to 3 show processes for fabricating a specimen for explanation of the preferred embodiment of FIG. 1. FIG. 4 shows a top plane view. FIGS. 1 to 3 show sectional views taken along the line A–A' of FIG. 4. In FIG. 1, a silicon oxide film ($SiO_2$) 2 with a thickness of more or less 500 nm is formed on a silicon substrate 1, and a silicon nitride film ($Si_3N_4$) 3 with a thickness of more or less 50 nm and a silicon oxide film 4 with a thickness of more or less 800 nm are laminated thereon. The thickness of the silicon nitride film 3 at the present time must be equal to the thickness capable of etching. The thickness of the silicon oxide film 4 also must be set in order for residual film to remain after CMP polishing finishes, although it depends on the processing time of phosphoric acid etching, discussed later.

In FIG. 2, the silicon oxide film 4 is etched by CMP until the etching thickness becomes more or less 500 nm, in order for the residual film of the silicon oxide film 4 to become more or less 300 nm. As previously explained, polishing is necessary so that the silicon oxide film 4 remains, namely, in order for the silicon nitride film 3 of lower layers not to be exposed. At this time, as shown in FIG. 2, there may be scratches having various shapes and depths on the surface of the silicon oxide film 4. For example, scratches such as a deep scratch 5 and a shallow scratch 6 may exist. It is quite difficult to separately detect the scratches 5 and 6 from the surface of the present specimen.

In FIG. 3, a 170° C. phosphoric acid ($H_3PO_4$) treatment is processed until the silicon nitride film 3 disappears completely. Compared to the silicon nitride film, the silicon oxide film has a quite small stch rate and high selectivity when exposed to hot phosphoric acid treatment, thus only the silicon nitride film 3 exposed by the deep scratch 5 is etched. Further, the silicon nitride film 3 of the deep scratch 5, the depth of which reaches the silicon oxide film 2, disappears completely, thus exposing the silicon oxide film 2.

Owing to the etching process, as shown in FIG. 4, observation of the scratch, the depth of which is more that the depth of the residual film, becomes easy using an optical microscope or an optical measuring tool, since the scratch 5, the depth of which is more than the depth of the silicon oxide film 4, becomes obvious. Additionally, the contrast between the scratch 5 and portions other than the scratch 5 become obvious. As a result, it becomes possible to analyze the scratch, and further to analyze the relative relationship between a failure and a yield rate and the like.

Figure 5:
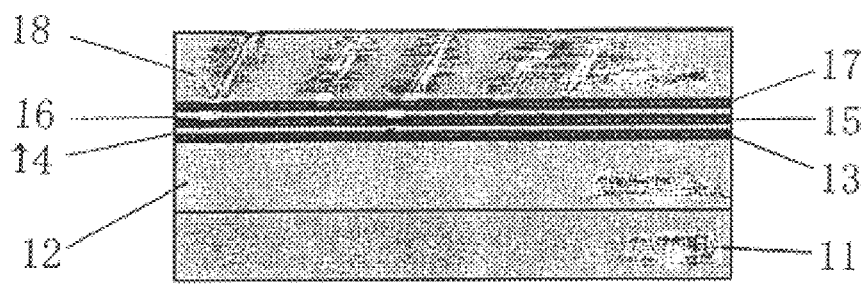
FIG. 5 is a sectional view of a fabricated specimen for explanation of the second preferred embodiment of the present invention, and illustrates a structure in which the top layer of the silicon oxide film is formed.
Figure 6:
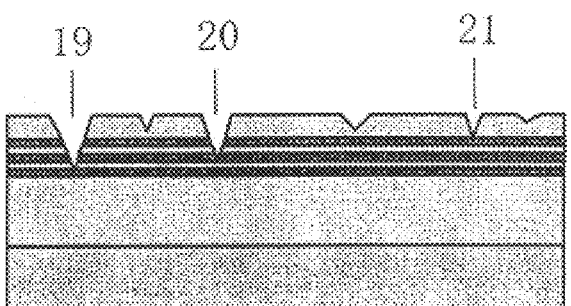
FIG. 6 is a sectional view of a fabricated specimen for explanation of the second preferred embodiment of the present invention, and illustrates scratches caused after CMP polishing.
Figure 7:
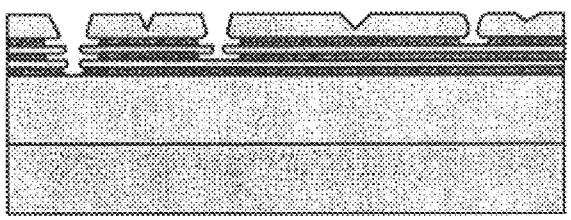
FIG. 7 is a sectional view of a fabricated specimen for explanation of the second preferred embodiment of the present invention, and illustrates etching of scratched portions.
Figure 8:
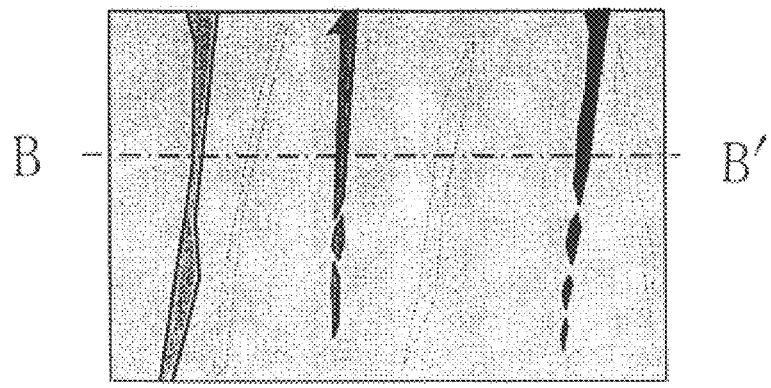
FIG. 8 is a sectional view of a fabricated specimen for explanation of the second preferred embodiment of the present invention, and illustrates a shape after etching the scratched portions.

FIGS. 5 to 7 show a fabrication process of a specimen, for explanation of the second preferred embodiment, and FIG. 8 shows a top plane view. FIGS. 5 to 7 show sectional views taken along the line B–B' of FIG. 8. In FIG. 5, a silicon oxide film 12 having a thickness of more or less 500 nm is formed on a silicon substrate 11. Following this, a silicon nitride film 13, a silicon oxide film 14, a silicon nitride film 15, a silicon oxide film 16, and a silicon nitride film 17, each thickness of which is more or less 10 nm, are then formed. Finally a silicon oxide film 18, the thickness of which is more or less 500 nm is formed, for polishing by CMP.

The thickness of laminated films of the silicon nitride film 13, the silicon oxide film 14, the silicon nitride film 15, the silicon oxide film 16, and the silicon nitride film 17 depends on the depth of the scratch, etching process time using the phosphoric acid or a CMP condition, and so forth. It is required that the thickness of a silicon oxide film 18 be set in order for residual film to exist when CMP polishing finishes.

In FIG. 6, the silicon oxide film 18 is etched by CMP polishing until the etching thickness becomes more or less 500 nm, and the thickness of the residual film of the silicon oxide film 4 is defined as more or less 300 nm. CMP polishing must be executed in order for a residual part of the silicon oxide film 18 to exist, that is to say, for the silicon nitride film 17 not to be exposed. At this stage, as shown in FIG. 6, it is impossible to detect separately scratches 19 to 21 on the surface of the present specimen, although it was thought that there may be scratches 19 to 21 on the surface of the silicon oxide film 18 having various shapes and depths. In FIG. 7, the 170° C. phosphorous acid process is undertaken until the silicon nitride film 15 and the silicon nitride film 13 disappear completely (necessary time for etching a nitride film having a thickness of 10 nm). Compared with the silicon nitride film, the silicon oxide film has an extremely small hot phosphorous acid stch rate and high selectivity, thus only each nitride film of the portion exposed by the scratches 19 to 21 is etched.

The scratches 19 to 21 reach to the silicon nitride films 13, 15, and 17 corresponding to respective depths thereof, the nitride films thereof disappear completely, and thus the oxide film of the lower layers of the nitride films is exposed. As shown in FIG. 8, in accordance with the etching process, the scratches, the depth of which is deeper than the depth of the silicon oxide film 18 and reaches to the silicon nitride films 13, 15, and 17, become exposed and the contrast difference becomes clear, corresponding to the depth of the scratch. Thus it becomes possible to observe the scratch easily, the depth of which is deeper than the depth of the residual film, using an optical microscope or an optical measuring tool.

In the scratches produced by CMP polishing of the insulating films between layers, it becomes possible to select a particle from a pattern failure and the like using the contrast of a scratch having a predetermined depth, to allow obvious identification from other portions. Thus, it becomes possible to observe the scratch using an optical microscope or an optical measuring tool. In this manner, it becomes possible to investigate the correlation between the scratch and the yield rate, to examine a mechanism that causes the scratch, and further to devise a countermeasure to the scratch.

What is claimed is:

1. A method for detecting a scratch of an insulating film in a semiconductor device, comprising:

preparing a silicon substrate on which a first insulating film, a silicon nitride film, and a second insulating film are layered in that order, wherein the silicon nitride film is thinner than the first insulating film in thickness;

polishing the second insulating film by a chemical mechanical polishing process; and removing the silicon nitride film exposed by the scratch after the chemical mechanical polishing process.

2. A method for detecting a scratch of an insulating film according to claim 1, wherein the second insulating film is a silicon oxide film.

3. A method for detecting a scratch of an insulating film according to claim 1, wherein the silicon nitride film is removed by using a hot phosphorous acid.

4. A method for detecting a scratch of an insulating film according to claim 1, wherein the second insulating film is polished so as to remain on the silicon nitride film, the remaining second insulating film being thicker than the silicon nitride film.

5. A method for detecting a scratch of an insulating film according to claim 3, wherein the phosphorus acid is heated approximately at 170 degrees Centigrade.

6. A method for detecting a scratch of an insulating film in a semiconductor device, comprising:

preparing a silicon substrate on which a first insulating film, a plurality of intermediate films, and a second insulating film are layered in that order, wherein the plurality of intermediate films includes two or more silicon nitride films with an insulating film formed between each pair of silicon nitride films, and the plurality of intermediate films is thinner the first insulating film in thickness;

polishing the second insulating film by a chemical mechanical polishing process; and removing the silicon nitride films exposed by the scratch after the chemical mechanical polishing process.

7. A method for detecting a scratch of an insulating film according to claim 6, wherein the second insulating film is a silicon oxide film.

8. A method for detecting a scratch of an insulating film according to claim 6, wherein each of the exposed silicon nitride films is removed by using a hot phosphorous acid.

9. A method for detecting a scratch of an insulating film according to claim 6, wherein the second insulating film is polished so as to remain on the plurality of intermediate films, the remaining second insulating film being thicker than the plurality of intermediate films.

10. A method for detecting a scratch of an insulating film according to claim 6, wherein each the insulating films formed between the silicon nitride films is a silicon oxide film.

11. A method for detecting a scratch of an insulating film according to claim 8, wherein the phosphorous acid is heated approximately at 170 degrees Centigrade.

* * * * *